United States Patent [19]

Tanabe

[11] 4,094,887
[45] June 13, 1978

[54] PROCESS FOR PREPARING CYCLIC ETHERS

[75] Inventor: Yasuo Tanabe, Kurashiki, Japan

[73] Assignee: Mitsubishi Chemical Industries, Ltd., Tokyo, Japan

[21] Appl. No.: 774,899

[22] Filed: Mar. 7, 1977

[30] Foreign Application Priority Data

Mar. 16, 1976 Japan .................................. 51-28453

[51] Int. Cl.$^2$ .......................................... C07D 307/08
[52] U.S. Cl. ............................................... 260/346.11
[58] Field of Search ..................... 260/346.1 R, 346.11

[56] References Cited

U.S. PATENT DOCUMENTS

| 4,005,112 | 1/1977 | Smith | 260/346.1 R |
| 4,005,113 | 1/1977 | Smith | 260/346.1 R |
| 4,010,171 | 3/1977 | Smith | 260/346.1 R |
| 4,011,244 | 3/1977 | Smith | 260/346.1 R |

FOREIGN PATENT DOCUMENTS 1,170,222  11/1969  United Kingdom .......... 260/346.1 R

*Primary Examiner*—Richard L. Raymond
*Attorney, Agent, or Firm*—Bierman & Bierman

[57] ABSTRACT

This invention relates to a process for preparing tetrahydrofuran or dihydrofuran by reacting an acetic acid ester of 1,4-butanediol or 1,4-dihydroxybutene-2 and water in the presence of an acid catalyst with a high yield. The process is characterized in that the reaction is carried out in two separate reaction zone in combination with a plurality of distilling columns and a part of reaction product is recycled to a predetermined position of the reaction zone.

10 Claims, 1 Drawing Figure

U.S. Patent  June 13, 1978  4,094,887
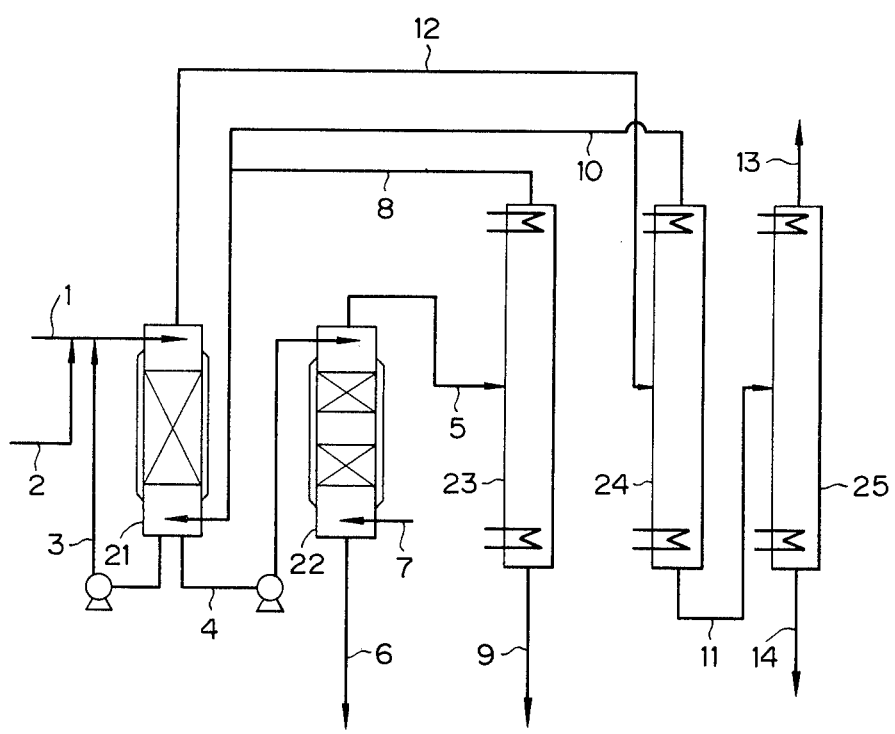

PROCESS FOR PREPARING CYCLIC ETHERS

BRIEF SUMMARY OF THE INVENTION

This invention relates to a process for preparing cyclic ethers directly from acetic acid esters of 1,4-glycols. More particularly, it relates to a process for preparing tetrahydrofuran or dihydrofuran from an acetic acid ester of 1,4-butanediol or 1,4-dihydroxybutene-2.

Tetrahydrofuran is known to be useful as a solvent for various kinds of materials, particularly polymeric materials such as polyvinyl chloride, polyvinylidene chloride, etc., and has been heretofore produced by a variety of processes. Typical of the processes are a process for catalytically hydrogenating furan obtained by decarbonization of furfural, a process wherein butynediol obtained by reacting acetylene and formaldehyde is hydrogenated to give butanediol, which is then dehydrated for ring formation, and a process which comprises reacting a diacetic acid ester of 1,4-butanediol with water in the presence of an acid catalyst. (Refer to British Patent 1170222).

It is known that production of a cyclic ether, particularly tetrahydrofuran, from an acetic acid ester of 1,4-glycol is conveniently feasible when water required for the reaction is used in an excess of that theoretically required and fed water as steam together with the starting ester to contact with a solid acid catalyst, followed removing the cyclic ether being produced in gas phase from the reaction system. (Refer to Offenlegungsschrift Nos. 2415663 and 2456780).

However, a large amount of water is contained in the reaction product discharged from the reactor when an excessive amount of water is used for the reaction. Since tetrahydrofuran and water readily form an azeotropic mixture, the reaction product must be repeatedly distilled in order to recover anhydrous tetrahydrofuran, thus requiring additional and complicate steps.

On the other hand, when the amount of water employed is reduced, there is a tendency of lowering the rate of conversion to some extent though the reaction product contains a reduced amount of water. This is very disadvantageous from an industrial point of view.

I have made an intensive study of a process, in which a reaction product can be obtained with high content of a cyclic ether and can be purified by a simple distillation procedure, and succeeded in obtaining a substantially water-free and high quality cyclic ether by a process which uses a reaction system including, in combination, two reaction zones and a plurality of distilling columns and in which part of a reaction product is fed back to a particular reaction zone.

An object of the present invention is to provide a process for preparing high quality cyclic ethers directly from acetic acid esters of 1,4-glycols in an industrially advantageous manner.

Another object is to produce a high quality cyclic ether substantially free from water by using a two reaction vessels in combination with a plurality of distillation columns.

The above object can be achieved according to the present invention by a process wherein a cyclic ether is prepared by interacting an acetic acid ester of 1,4-butanediol or 1,4-dihydroxybutene-2 and water in the presence of an acid catalyst in two reaction zones arranged in series, the process comprising the step of (a) continuously feeding to the first reaction zone the acetic acid ester and a mixture of the cyclic ether and water recycled from a first and a second distilling columns to effect the catalytic reaction; (b) withdrawing a gaseous mixture composed of a produced cyclic ether, water and acetic acid from the first reaction zone and feeding the gaseous mixture to the second distilling column; (c) feeding the solution discharged from the first reaction zone and fresh water to the second reaction zone and withdrawing the resulting a gaseous mixture of the cyclic ether, water and acetic acid from the second reaction zone; (d) feeding the gaseous mixture discharged from the second reaction zone to the first distilling column and recycling a mixture of the cyclic ether and water distilled from the top of the first distilling column to the first reaction zone while discharging acetic acid as a bottom product; (e) feeding a mixture of the cyclic ether and water distilled from the top of the second distilling column to the first reaction zone and at the same time, taking out a substantially water-free cyclic ether-containing product from the bottom of the second distilling column; and (f) subjecting said product obtained in the step (e) to further distillation to obtain the cyclic ether.

BRIEF DESCRIPTION OF THE DRAWING

The drawing is a flow chart and represents an embodiment of the present invention and is not meant to limit the subject matter as set forth in the claims.

DETAILED DESCRIPTION OF THE INVENTION

The acetic acid esters of 1,4-butanediol or 1,4-dihydroxybutene-2 usable as the starting material in the present invention include monoacetic acid esters and diacetic acid esters of 1,4-glycols such as 1,4-diacetoxybutane, 1-hydroxy-4-acetoxybutane, 1,4-diacetoxybutene-2, 1-hydroxy-4-acetoxybutene-2.

These acetic acid esters can be prepared by known various processes. For example, the acetoxylation reaction of butadiene, acetic acid and oxygen or molecular oxygen-containing gas in the presence of a palladium-base catalyst can be conducted and 1,4-diacetoxybutene-2 and 1-hydroxy-4-acetoxybutene-2 are separated from the acetoxylation product. Further, 1,4-diacetoxybutane and 1-hydroxy-4-acetoxybutane are obtainable by hydrogenating the above-mentioned acetoxylation reaction product in the presence of a nickel- or palladium-base catalyst and recovering from the hydrogenation product.

Such product contains mainly the above-mentioned acetic acid esters of glycol, but, depending on the reaction conditions or the manner of purification, the acetic acid esters may contain other isomers such as acetic acid esters of 1,2- or 1,3-glycol. In some cases, the acetic acid esters may contain butyl acetate and acetic acid secondarily produced by the hydrogenation step. It is preferable to use the acetic acid esters of 1,4-glycols, especially diacetic ester of 1,4-butanediol having a purity of above 99.5%.

1-hydroxy-4-acetoxybutane suitable as the starting material may be obtained by partial hydrolysis of the above-indicated 1,4-diacetoxybutane. In the practice of the invention, however, it is preferable to use 1-hydroxy-4-acetoxybutane which is prepared by reacting propylene with molecular oxygen and acetic acid in the presence of a palladium catalyst to give allyl acetate, subjecting the allyl acetate to OXO reaction to obtain 4-acetoxybutylaldehyde and then hydrogenating the aldehyde. The thus obtained 1-hydroxy-4-acetoxybutane may contain 2-methyl-3-acetoxypropyl alcohol which is derived from 2-methyl-3-acetoxypropionaldehyde secondarily produced upon the oxo reaction. However, the 2-methyl-3-acetoxypropyl alcohol does not appear to hinder the process of the invention.

The acid catalysts useful in the process of this invention should be those which are non-volatile, including liquid acids and solid acids. Examples of the liquid acids include inorganic acids such as sulfuric acid, phosphoric acid, etc., organic sulfonic acids such as benzene-sulfonic acid, toluenesulfonic acid, trifluoromethanesulfonic acid, etc. Of these, sulfuric acid is most preferable from a viewpoint of economy. Examples of the solid acids include activated clay, silica-titania, silica-alumina, silica-zirconia, chromia-alumina, silica-magnesia, natural and synthetic zeolites, a strong acid cation exchange resin and the like.

Though the amount of the acid catalyst may vary depending on the kind of the acid, the liquid acid is generally used in an amount of 0.01–100 parts by weight per part of the starting acetic acid ester. With the solid acid, it is frequently used as a catalyst bed packed in a column and is general to be employed in a liquid hourly space velocity (L.H.S.V. $hr^{-1}$) of 0.001–10 though depending on the capacity of apparatus and the activity of the catalyst.

According to this invention water from any sources may be employed as one of the starting materials and it is desired to be free of chlorine ions. Preferably, water is fed as steam.

The process of the present invention will be particularly illustrated with reference to the accompanying drawing.

In the flow chart 21 and 22 represent the first and the second reaction zones respectively, 23 and 24 represent the first and the second distilling columns, and 25 represents a purifying column.

In the practice of the invention, the reaction is conducted in two reaction zones 21 and 22 arranged in series. The type and detail of such reaction zones are not critical and any reaction apparatus which ensure satisfactory gas-liquid contact may be used. Embodiments of the mode of reaction are as follows. (a) The reaction conveniently carried out by using a bubble column or an agitated reactor containing a catalyst (a liquid acid or a solid acid suspension bed), to which a liquid acetic acid ester of glycol is fed to form a liquid phase and simultaneously water or steam is introduced from the lower part of the column or reactor. The reaction may be conducted, if necessary, under exterior heating conditions. A multi-stage bubble column or a packed bubble column may be used as the bubble column. (b) To a column packed with a porcelain or metal packing such as Raschig rings, Berl saddles and Intalox saddles fed are a starting liquid acetic acid ester and a non-volatile acid catalyst. At the same time, steam is fed to the column for the reaction. Though the starting liquid materials and steam may be passed downwardly from the top of the column or upwardly from the bottom of the column in a vapor-liquid concurrent flow, it is preferable to countercurrently contact the vapor and the liquids with each other and most preferably, the starting liquid materials are passed downwardly from the top while the steam is fed upwardly. The resulting liquid reaction product, if necessary, may be circulated externally. The gas phase containing a produced cyclic ether and acetic acid is discharged from the reaction zone and fed to a distillation column.

In the above case, a multi-stage packed column may be used. Further, the reaction may be effected by a fixed bed system packing therein a solid acid catalyst instead of the packing.

The two reaction zones may be established by properly combining the reactors as mentioned above. That is, two reactors may be used to define the two reaction zones, or one reactor which is separated by a suitable means to define two reaction zones may be used. In some case, the two reaction zones may be each constituted of a multi-stage reaction zone.

In the accompanying drawings, the reaction zones are indicated at 21 and 22, and a packed column in the second reaction zone consists of two reaction zones. These reactors are essentially required to be acid proof. When, for example, a solid acid is used as catalyst, a SUS 316 stainless steel reactor is preferably employed. With a liquid acid, a SUS 316 stainless steel reactor is used when the reaction temperature is relatively low and a Hastelloy- or glass-lined reactor is used when the reaction temperature is relatively high.

The reaction temperature of the first and the second reaction zones is generally in the range of from 100° to 200° C, preferably 120° to 160° C. With the liquid acid catalyst, relatively low temperatures within the above-defined range are preferred, while, with the solid acid catalyst, relatively high temperatures above 120° C are preferably used.

The reaction pressure operable in the practice of the invention ranges from atmospheric pressure to 3 $kg/cm^2G$, preferably atmospheric to 1 $kg/cm^2G$.

Referring to the drawing, a starting acetic acid ester is fed to the reactor 21 through a pipe 1, and a liquid acid such as sulfuric acid serving as catalyst is fed to the reactor 21 through a pipe 2 with or without a reaction solution recycled through a pipe 3. To the reactor 21 are also fed through pipes 8 and 10 mixture of water and cyclic ether which are distilled off from the first and the second distilling columns 23 and 24, respectively, in the form of a gaseous phase, by which the catalytic reaction takes place by a countercurrent manner. The liquid reaction product discharged from the bottom of the reactor 21 and containing the unreacted starting materials, acid catalyst, acetic acid and the like is fed through a pipe 4 to the second reactor 22, to which fresh water is fed through a pipe 7 in the form of steam.

While, a gaseous mixture of the ether, water and acetic acid discharged from the reactor 21 is passed through a pipe 12 into the second distilling column 24 for distillation. The azeotropic gas mixture of water and the cyclic ether distilled out from the top of the column is recycled to the reactor 21 through the pipe 10 as mentioned hereinbefore. From the bottom of the column is obtained a distillate which contains acetic acid and the cyclic ether and which is substantially free of water. The distillate is passed into a purifying column 25 through a pipe 11 to give a pure cyclic ether product which is obtained from the top of the column 25 through a pipe 13. From the bottom of the column 25 is withdrawn a bottom containing acetic acid through a pipe 14.

The gaseous mixture containing the cyclic ether, water and acetic acid distilled from the top of the reactor 22 is fed to the first distilling column 23 for separating acetic acid therefrom. The cyclic ether-water mixture discharged from the top of the column is recycled to the first reactor 21 while discharging the acetic acid fraction from the bottom of the column. While, it is necessary to suitably withdraw from the bottom of the second reactor 22 through the pipe 6 the reaction solution mainly containing the catalyst and acetic acid in an amount corresponding to that of the starting materials to be fed to the reaction system.

The type of distilling columns and the purifying column may be any of conventional columns ordinarily employed for distillation. A multi-stage distilling column or a packed distilling column made of stainless steel SUS 316 is used for the purpose.

The distillation is generally conducted under conditions concluding number of the theoretical plates of 5–20, a pressure of atmospheric to 3 kg/cm$^2$G, and a reflux ratio of 0.5–10.

If desired, the second distilling column may be composed of two distilling columns. That is, a mixture of cyclic ether and water is distilled off in one of the distilling columns while withdrawing acetic acid as a bottom, and the distilled mixture is then fed to the other column (which is desired to have a pressure higher by 2–15 kg/cm$^2$ than that of the first-mentioned column) to distil the cyclic ether and water in gas phase while discharging a substantially water-free cyclic ether from the bottom of the second-mentioned column. The distilled cyclic ether and water are fed to the first reactor.

As will be understood from the foregoing descriptions, the starting acetic acid ester is catalytically reacted with a small amount of water in the first reaction zone, so that the gaseous mixture discharged from the first reaction zone has a high concentration of the cyclic ether. Accordingly, a simple distillation operation is sufficient to separate the cyclic ether from the gaseous mixture to obtain a substantially water-free cyclic ether distillate. On the other hand, steam is fed to the second reaction zone in an amount much larger than the starting ester, with the attendant high rate of conversion of the ester. The gaseous mixture discharged from the second reaction zone is distilled in the first distilling column to separate acetic acid therefrom and a substantially all amount of the cyclic ether produced on the second reaction zone is recycled to the first reaction zone. From the above it will be understood that the process of the invention is much improved in efficiency without any losses of the starting esters.

The present invention will be particularly illustrated by way of the following example, which should not be construed as limiting the scope of the present invention in any manner.

EXAMPLE 1

The reaction was conducted using the reaction system shown in the accompanying drawing.

There were used as the reactors 21 and 22 Hastelloy reactor tubes each equipped with a heating jacket and having an inner diameter of 100 mm and a height of 7.5 m. Each of the reaction tubes was packed with 60 l of porcelain balls (with a diameter of 5 mm).

Pressure saturated steam of 140° C was passed into the jacket of the first reactor, to which were fed from the pipes 1 and 2, 1,4-diacetoxybutane and sulfuric acid which had been preheated to 140° C, in amounts of 17400 g/hr and 980 g/hr, respectively. At the same time, 6020 g/hr of a gas distilled from the first distilling column 23 and 2590 g/hr of a gas distilled from the second distilling column 24, both of which had been preheated up to 140° C, were fed from the bottom of the first reactor 21 through the pipes 8 and 10, respectively. 11490 g/hr of the gaseous mixture of tetrahydrofuran (THF), H$_2$O and acetic acid (AcOH) continuously discharged from the top of the first reactor 21 was passed into the second distilling column 24 through the pipe 12.

While, 15470 g/hr of the reaction solution containing the unreacted starting materials was continuously passed from the bottom of the first reactor 21 through the pipe 4 into the second reactor 22 which was heated by passing steam of 140° C through the jacket of the reactor 22 in the manner similar to the first reactor. To the second reactor 22 was simultaneously fed for the reaction 3560 g/hr of steam superheated to 140° C under atmospheric pressure through the pipe 7.

17500 g/hr of the gaseous mixture of THF, H$_2$O and AcOH discharged from the upper side of the second reactor 22 was fed to the first distilling column through the pipe 5 while withdrawing 1570 g/hr of a solution containing the unreacted materials, high boiling point materials and sulfuric acid from the bottom of the second reactor through the pipe 6.

The first distilling column was made of SUS 316 stainless steel, had an inner diameter of 100 mm and a height of 10 m, and was packed with the Dickson packing. The gaseous mixture fed from the pipe 5 was charged at 5 m below the top of the column and the distillation was effected at a reflux ratio of 1.5 under an atmospheric pressure. 6020 g/hr of the gas (containing 82.2 mol % of THF) from the top of the column was recycled to the first reactor through the pipe 8, while 11480 g/hr of a bottom containing a major proportion of acetic acid was discharged through the pipe 9.

The second distilling column was similar in construction to the first distilling column. In the second distilling column, the gaseous mixture fed from the first reactor through the pipe 12 was distilled at a reflux ratio of 2.0 under an atmospheric pressure. 2590 g/hr of a solution composed of a THF-H$_2$O azeotropic composition from the top of the column was passed into the first reactor through the pipe 10, while 8890 g/hr of a bottom was fed into the purifying column 25 through the pipe 11. The purifying column was constructed of similarly to the first distilling column and operated at a reflux ratio of 2.0 under an atmospheric pressure, thereby yielding 6850 g/hr of THF with a purity of 99.95% from the top of the column through the pipe 13. At the same time, 2040 g/hr of acetic acid was obtained from the bottom of the column through the pipe 14.

What is claimed is:

1. A process for preparing a cyclic ether by interacting an acetic acid ester of 1,4-butanediol or 1,4-dihydroxybutene-2 and water in the presence of a nonvolatile liquid acid catalyst in two reaction zones arranged in series, which process comprises the steps of:
    (a) continuously feeding to the first reaction zone said acetic acid ester and a mixture of the cyclic ether and water recycled from a first and a second distilling columns to effect the catalytic reaction,
    (b) withdrawing a mixed gas composed of a produced cyclic ether, water and acetic acid from the first reaction zone and feeding said mixed gas to the second distilling column,
    (c) feeding the solution discharged from the first reaction zone and fresh water to the second reaction zone for further catalytic reaction and withdrawing the resulting mixed gas composed of the cyclic ether, water and acetic acid from said second reaction zone,
    (d) feeding for distillation the mixed gas discharged from the second reaction zone to the first distilling column and recycling a mixture of the cyclic ether and water distilled from the column top to the first reaction zone while discharging acetic acid as a bottom product, (e) feeding a mixture of the cyclic ether and water distilled from the top of the second distilling column to the first reaction zone and at the same time, taking out a substantially water-free cyclic ether-containing product from the bottom of the second distilling column, and (f) subjecting said product obtained in the step (e) to further distillation to obtain the cyclic ether.

2. A process for preparing a cyclic ether according to claim 1, wherein said reaction is carried out at a temperature of from 100° to 200° C and under a pressure of from atmospheric to 3 Kg/cm$^2$G.

3. A process for preparing a cyclic ether according to claim 1, wherein said catalyst is an inorganic acid selected from the group consisting of sulfuric acid and phosphoric acid.

4. A process for preparing a cyclic ether according to claim 1, wherein said catalyst is sulfuric acid.

5. A process for preparing a cyclic ether according to claim 1, wherein said catalyst is an organic sulfonic acid selected from the group consisting of benzenesulfonic acid, toluenesulfonic acid and trifluoromethanesulfonic acid.

6. A process for preparing a cyclic ether according to claim 1, wherein said mixture of the cyclic ether and water is fed in a gaseous phase in step (a).

7. A process for preparing a cyclic ether according to claim 1, wherein said acetic acid ester is an diacetic acid ester of 1,4-butanediol and said cyclic ether is tetrahydrofuran.

8. A process for preparing a cyclic ether according to claim 1, wherein the fresh water employed in step (c) is steam.

9. A process for preparing a cyclic ether according to claim 1, wherein the first and the second distilling columns are operated under the conditions of the number of the theoretical plates of from 5 to 20, under a pressure of from atmospheric to 3 kg/cm$^2$G and at a reflux ratio of from 0.5 to 10.

10. A process for preparing a cyclic ether according to claim 1, wherein the mixed gas composed of a produced cyclic ether, water and acetic acid from the first reaction zone in step (b) is subjected to distillation to separate liquid acetic acid as a bottom residue and a gaseous mixture of cyclic ether and water as a top fraction, the latter being supplied to the second distillation column.

* * * * *